US008765446B2

(12) United States Patent
Lee et al.

(10) Patent No.: US 8,765,446 B2
(45) Date of Patent: Jul. 1, 2014

(54) RECOMBINANT MUTANT MICROORGANISMS HAVING INCREASED ABILITY TO PRODUCE ALCOHOLS AND METHOD OF PRODUCING ALCOHOLS USING THE SAME

(75) Inventors: Sang Yup Lee, Daejeon (KR); Yu-Sin Jang, Daejeon (KR); Joung Min Lee, Gangwon-do (KR); Jung Ae Im, Daejeon (KR); Hyohak Song, Daejeon (KR)

(73) Assignees: Korea Advanced institute of Science and Technology, Daejeon (KR); Biofuelchem Co., Daejeon (KR); GS Caltex Corporation, Seoul (KR)

( * ) Notice: Subject to any disclaimer, the term of this patent is extended or adjusted under 35 U.S.C. 154(b) by 0 days.

(21) Appl. No.: 13/497,736

(22) PCT Filed: Sep. 21, 2010

(86) PCT No.: PCT/KR2010/006510
§ 371 (c)(1),
(2), (4) Date: Aug. 20, 2012

(87) PCT Pub. No.: WO2011/037414
PCT Pub. Date: Mar. 31, 2011

(65) Prior Publication Data
US 2012/0301936 A1 Nov. 29, 2012

(30) Foreign Application Priority Data

Sep. 22, 2009 (KR) .................. 10-2009-0089826
Sep. 22, 2009 (KR) .................. 10-2009-0089827

(51) Int. Cl.
*C12N 1/20* (2006.01)
*C12N 15/74* (2006.01)
*C12N 9/02* (2006.01)
*C12N 15/00* (2006.01)
*C12P 7/16* (2006.01)
*C12Q 1/26* (2006.01)
*C07H 21/04* (2006.01)

(52) U.S. Cl.
USPC .......... 435/252.3; 435/25; 435/160; 435/189; 435/471; 435/320.1; 536/23.1; 536/23.2

(58) Field of Classification Search
None
See application file for complete search history.

(56) References Cited

U.S. PATENT DOCUMENTS

| 2007/0259410 A1 | 11/2007 | Donaldson et al. | |
| 2008/0293125 A1 | 11/2008 | Subbian et al. | |
| 2011/0027845 A1 | 2/2011 | Lee et al. | |
| 2013/0095542 A1* | 4/2013 | Pereira et al. | 435/157 |

FOREIGN PATENT DOCUMENTS

| WO | 2008052596 A1 | 5/2008 |
| WO | 2008052973 A2 | 5/2008 |
| WO | 2008080124 A2 | 7/2008 |
| WO | 2008097064 A1 | 8/2008 |

OTHER PUBLICATIONS

Atsumi et al. Metabolic engineering for advanced biofuels production from *Escherichia coli*, (2008, Epub Sep. 12, 2008), Current Opinion in Biotechnology, 19: 414-419.*
Mathews et al. Metabolic pathway engineering for enhanced hydrogen production, (Epub Jun. 17, 2009), International Journal of hydrogen energy, 34: 7404-7416, 2009.*
Matsumura et al. Continuous butanol/Isopropanol fermentation in down-flow column reactor coupled with pervaporation using supported liquid membrane, (1992), Biotechnology and Bioengineering, 39: 148-156.*
Shaheen, et al.,"Comparative Fermentation Studies of Industrial Strains Belonging to Four Species of Solvent-Producing Clostridia," Journal of Mol. Microbiol. Biotechnol., 2000, pp. 115-124, vol. 2.
Nair, et al.,"Noleculart Characterization of an Aldehyde/Alcohol Dehydrogenase Gene from *Clostridium acetobutylicum* ATCC 824," Journal of Bacteriology, 1994, pp. 871-885, col. 176.
Harris, et al.,"Characterization of Recombinant Strains of the *Clostridium acetobutylicim* Butyrate Kinase Inactivation Mutant: Need for New Phenomenological Models for Solventogenesis and Butanol Inhibition?" Biotechnol. Bioeng., 2000, pp. 1-11, vol. 67.
Ezeji et al., "Acetone butanol ethanol (ABE) production from concentrated substrate: reduction in substrate inhibition by fed-batch technique and product inhibition by gas stripping," Appl. Microbiol. Biotechnol., 2004, pp. 653-658, vol. 63.
Nair, et al.,"Expression of Plasmid-Encoded aad in *Clostridium acetobutylicum* M5 Restores Vigorous Butanol Production," Journal of Bacteriology, 1994, pp. 5843-5846, vol. 176.
Jiang, et al.,"Disruption of the acetoacetate decarboxylase gene in solvent-producing *Clostridium acetobutylicum* increases the butanol ratio," Metabolic Engineering, 2009, pp. 284-291, vol. 11.
Liao, et al.,"Engineered Synthetic Pathway for Isopropanol Production in *Escherichia coli*," Applied and Environmental Microbiology, 2007, pp. 7814-7818, vol. 73.

* cited by examiner

*Primary Examiner* — Iqbal H Chowdhury
(74) *Attorney, Agent, or Firm* — Tristan A. Fuierer; Andrew D. Gerschutz; Moore & Van Allen, PLLC

(57) ABSTRACT

The present invention relates to recombinant mutant microorganisms having an increased ability to produce alcohol and a method of producing alcohol using the same, and more particularly to recombinant mutant microorganisms which have an increased ability to produce butanol, ethanol, isopropanol or mixed alcohols, which can be used as fuel, while producing little or no producing acetone as a byproduct, and to a method of producing butanol, ethanol, isopropanol or mixed alcohols using the same. The inventive recombinant mutant microorganisms having an increased ability to produce butanol or mixed alcohols and to remove acetone are those in which genes that encode enzymes involved in producing butanol from butyryl-CoA or butylaldehyde and in producing isopropanol from acetone were amplified or introduced in host microorganisms. The recombinant mutant microorganisms produce little or no byproducts such as acetone and can have an increased ability to produce alcohols, as a result of manipulating metabolic pathways. Thus, the recombinant mutant microorganisms are useful for industrial production of butanol or mixed alcohols comprising butanol and isopropanol.

16 Claims, 2 Drawing Sheets

SEQUENCE LISTING

<160> NUMBER OF SEQ ID NOS: 34

<210> SEQ ID NO 1
<211> LENGTH: 36
<212> TYPE: DNA
<213> ORGANISM: Artificial Sequence
<220> FEATURE:
<223> OTHER INFORMATION: Synthetic Construct

<400> SEQUENCE: 1
ggccccaagc ttagaatgaa gtttcttatg cacaag         36

<210> SEQ ID NO 2
<211> LENGTH: 36
<212> TYPE: DNA
<213> ORGANISM: Artificial Sequence
<220> FEATURE:
<223> OTHER INFORMATION: Synthetic Construct

<400> SEQUENCE: 2
aaactgcagt ctaactaacc tcctaaattt tgatac         36

<210> SEQ ID NO 3
<211> LENGTH: 31
<212> TYPE: DNA
<213> ORGANISM: Artificial Sequence
<220> FEATURE:
<223> OTHER INFORMATION: Synthetic Construct

<400> SEQUENCE: 3
ccaagcttcg acttttaac aaaatatatt g               31

<210> SEQ ID NO 4
<211> LENGTH: 32
<212> TYPE: DNA
<213> ORGANISM: Artificial Sequence
<220> FEATURE:
<223> OTHER INFORMATION: Synthetic Construct

<400> SEQUENCE: 4
ccaagcttga cattaaaaaa ataagagtta cc             32

<210> SEQ ID NO 5
<211> LENGTH: 31
<212> TYPE: DNA
<213> ORGANISM: Artificial Sequence
<220> FEATURE:
<223> OTHER INFORMATION: Synthetic Construct

<400> SEQUENCE: 5
aaaactgcag atgaaaggtt ttgcaatgct a              31

<210> SEQ ID NO 6
<211> LENGTH: 36
<212> TYPE: DNA
<213> ORGANISM: Artificial Sequence
<220> FEATURE:
<223> OTHER INFORMATION: Synthetic Construct

<400> SEQUENCE: 6
cccccggggg tgtataatcc tccatgatct attatg         36

<210> SEQ ID NO 7
<211> LENGTH: 35
<212> TYPE: DNA
<213> ORGANISM: Artificial Sequence

```
<220> FEATURE:
<223> OTHER INFORMATION: Synthetic Construct

<400> SEQUENCE: 7
cccccggggg ccttctacac atttaggatt cttac                                35

<210> SEQ ID NO 8
<211> LENGTH: 69
<212> TYPE: DNA
<213> ORGANISM: Artificial Sequence
<220> FEATURE:
<223> OTHER INFORMATION: Synthetic Construct

<400> SEQUENCE: 8
aattgcatgc taccgttcgt ataatgtatg ctatacgaag ttatcacacg gtttaacgac    60
ttaattacg                                                             69

<210> SEQ ID NO 9
<211> LENGTH: 70
<212> TYPE: DNA
<213> ORGANISM: Artificial Sequence
<220> FEATURE:
<223> OTHER INFORMATION: Synthetic Construct

<400> SEQUENCE: 9
atattctaga accgttcgta tagcatacat tatacgaagt tatccatgat tacgaattct    60
atgagtcgac                                                            70

<210> SEQ ID NO 10
<211> LENGTH: 36
<212> TYPE: DNA
<213> ORGANISM: Artificial Sequence
<220> FEATURE:
<223> OTHER INFORMATION: Synthetic Construct

<400> SEQUENCE: 10
aaaactgcag ccatggtcgc cagttaatag tttgcg                              36

<210> SEQ ID NO 11
<211> LENGTH: 30
<212> TYPE: DNA
<213> ORGANISM: Artificial Sequence
<220> FEATURE:
<223> OTHER INFORMATION: Synthetic Construct

<400> SEQUENCE: 11
aaaacccggg cgccgcatac actattctca                                     30

<210> SEQ ID NO 12
<211> LENGTH: 31
<212> TYPE: DNA
<213> ORGANISM: Artificial Sequence
<220> FEATURE:
<223> OTHER INFORMATION: Synthetic Construct

<400> SEQUENCE: 12
ctagccatgg agcatatggg agtgtgctaa g                                   31

<210> SEQ ID NO 13
<211> LENGTH: 30
<212> TYPE: DNA
<213> ORGANISM: Artificial Sequence
<220> FEATURE:
<223> OTHER INFORMATION: Synthetic Construct
```

<400> SEQUENCE: 13
cggccaacgc tcgcagtcag gtattatcat                                   30

<210> SEQ ID NO 14
<211> LENGTH: 36
<212> TYPE: DNA
<213> ORGANISM: Artificial Sequence
<220> FEATURE:
<223> OTHER INFORMATION: Synthetic Construct

<400> SEQUENCE: 14
gcgaatggcg agatgaacta gctgatattg ctataa                            36

<210> SEQ ID NO 15
<211> LENGTH: 35
<212> TYPE: DNA
<213> ORGANISM: Artificial Sequence
<220> FEATURE:
<223> OTHER INFORMATION: Synthetic Construct

<400> SEQUENCE: 15
acgtcccggg cgagtacagt ttcatccttc atatc                             35

<210> SEQ ID NO 16
<211> LENGTH: 26
<212> TYPE: DNA
<213> ORGANISM: Artificial Sequence
<220> FEATURE:
<223> OTHER INFORMATION: Synthetic Construct

<400> SEQUENCE: 16
ctgactgcga gcgttggccg attcat                                       26

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
tagttcatct cgccattcgc cattca                                       26

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
gaggataaag aatatacgca gg                                           22

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
ttgccgtcct aaactctgaa                                              20

<210> SEQ ID NO 20
<211> LENGTH: 22

<212> TYPE: DNA
<213> ORGANISM: Artificial Sequence
<220> FEATURE:
<223> OTHER INFORMATION: Synthetic Construct

<400> SEQUENCE: 20
cttcctttgg caattcaagt tc                                                22

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
gtggattatg aagcggtgca                                                   20

<210> SEQ ID NO 22
<211> LENGTH: 34
<212> TYPE: DNA
<213> ORGANISM: Artificial Sequence
<220> FEATURE:
<223> OTHER INFORMATION: Synthetic Construct

<400> SEQUENCE: 22
atatggatcc aagtgtactt ttattttcga aagc                                   34

<210> SEQ ID NO 23
<211> LENGTH: 37
<212> TYPE: DNA
<213> ORGANISM: Artificial Sequence
<220> FEATURE:
<223> OTHER INFORMATION: Synthetic Construct

<400> SEQUENCE: 23
aatccctcct ttccatttaa ggtaactctt attttta                                37

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct

<400> SEQUENCE: 24
gttaccttaa atggaaagga gggattaaaa tgaactct                               38

<210> SEQ ID NO 25
<211> LENGTH: 33
<212> TYPE: DNA
<213> ORGANISM: Artificial Sequence
<220> FEATURE:
<223> OTHER INFORMATION: Synthetic Construct

<400> SEQUENCE: 25
atatacgcgt ctaaacagcc atgggtctaa gtt                                    33

<210> SEQ ID NO 26
<211> LENGTH: 61
<212> TYPE: DNA
<213> ORGANISM: Artificial Sequence
<220> FEATURE:
<223> OTHER INFORMATION: Synthetic Construct

<400> SEQUENCE: 26

```
gatccactac ggccgtaaaa ataagagtta ccttaaatgg taactcttat tttttaatg    60 c                                                                   61

<210> SEQ ID NO 27
<211> LENGTH: 61
<212> TYPE: DNA
<213> ORGANISM: Artificial Sequence
<220> FEATURE:
<223> OTHER INFORMATION: Synthetic Construct

<400> SEQUENCE: 27
aattgcatta aaaaaataag agttaccatt taaggtaact cttattttta cggccgtagt    60
g                                                                   61

<210> SEQ ID NO 28
<211> LENGTH: 34
<212> TYPE: DNA
<213> ORGANISM: Artificial Sequence
<220> FEATURE:
<223> OTHER INFORMATION: Synthetic Construct

<400> SEQUENCE: 28
atatctgcag aagtgtactt ttattttcga aagc                                34

<210> SEQ ID NO 29
<211> LENGTH: 35
<212> TYPE: DNA
<213> ORGANISM: Artificial Sequence
<220> FEATURE:
<223> OTHER INFORMATION: Synthetic Construct

<400> SEQUENCE: 29
atatggatcc taataatgtt tagcttttct aacat                               35

<210> SEQ ID NO 30
<211> LENGTH: 35
<212> TYPE: DNA
<213> ORGANISM: Artificial Sequence
<220> FEATURE:
<223> OTHER INFORMATION: Synthetic Construct

<400> SEQUENCE: 30
atatggatcc taaggaggaa catattttat gaaag                               35

<210> SEQ ID NO 31
<211> LENGTH: 36
<212> TYPE: DNA
<213> ORGANISM: Artificial Sequence
<220> FEATURE:
<223> OTHER INFORMATION: Synthetic Construct

<400> SEQUENCE: 31
atatcggccg ttataatata actactgctt taatta                              36

<210> SEQ ID NO 32
<211> LENGTH: 33
<212> TYPE: DNA
<213> ORGANISM: Artificial Sequence
<220> FEATURE:
<223> OTHER INFORMATION: Synthetic Construct

<400> SEQUENCE: 32
atatcggccg ttatttatca cctctgcaac cac                                 33
```

```
<210> SEQ ID NO 33
<211> LENGTH: 20
<212> TYPE: DNA
<213> ORGANISM: Artificial Sequence
<220> FEATURE:
<223> OTHER INFORMATION: Synthetic Construct

<400> SEQUENCE: 33
cgggcctctt cgctattacg                                              20

<210> SEQ ID NO 34
<211> LENGTH: 30
<212> TYPE: DNA
<213> ORGANISM: Artificial Sequence
<220> FEATURE:
<223> OTHER INFORMATION: Synthetic Construct

<400> SEQUENCE: 34
atatcccggg ggaattgtga gcggataaca                                   30
```

RECOMBINANT MUTANT MICROORGANISMS HAVING INCREASED ABILITY TO PRODUCE ALCOHOLS AND METHOD OF PRODUCING ALCOHOLS USING THE SAME

CROSS-REFERENCE TO RELATED APPLICATIONS

This application is filed under the provisions of 35 U.S.C. §371 and claims the priority of International Patent Application No. PCT/KR2010/006510 filed on 21 Sep. 2010 entitled "Recombinant Mutant Microorganism with Increased Alcohol Production Ability, and Preparation Method of Alcohol Using Same" in the name of Sang Yup LEE, et al., which claims priority of Korean Patent Application Nos. 10-2009-0089826 and 10-2009-0089827 both filed on 22 Sep. 2009, all of which are hereby incorporated by reference herein in their entirety.

TECHNICAL FIELD

The present invention relates to recombinant mutant microorganisms having an increased ability to produce alcohol and a method of producing alcohol using the same, and more particularly to recombinant mutant microorganisms which have an increased ability to produce butanol, ethanol, isopropanol or mixed alcohols, which can be used as fuel, while producing little or no producing acetone as a byproduct, and to a method of producing butanol, ethanol, isopropanol or mixed alcohols using the same.

BACKGROUND ART

Alcohols such as butanol, ethanol, isopropanol and the like are currently used as industrial solvents and have a large market size. Bioethanol has already been used as transportation fuel for cars in USA and Brazil. In addition, butanol and isopropanol are likely to be actually used as transportation fuel for cars, and thus the demand therefor is expected to continue to increase. Butanol as transportation fuel has energy density similar to gasoline, and ethanol and isopanol have a motor octane number higher than butanol. Mixed alcohols comprising two or more selected from the group consisting of ethanol, isopropanol and butanol have the advantages of having an octane number higher than pure butanol and an energy density higher than ethanol. A process of producing these mixed alcohols simultaneously at a suitable ratio is more advantageous in terms of cost than a process of producing alcohols separately and then mixing the produced alcohols with each other.

The worldwide production of butanol ($C_4H_9OH$) is estimated to be about 1.1 million tons/year. Currently commercially available butanol is all produced by chemical synthesis. Butanol is chemically synthesized by the oxo process from propylene obtained from petroleum. Ethanol ($C_2H_5OH$) has been produced by fermentation of starches or sugars, and these days, alcoholic liquors are mostly produced by this fermentation process. Industrial ethanol is produced by the sulfuric acid hydrolysis process in which ethylene (ethane) obtained from petroleum is absorbed into sulfuric acid to prepare a sulfuric acid ester of ethanol which is then hydrolyzed, thereby obtaining ethanol together with diethyl ether, or the direction hydration process in which gaseous ethylene is allowed to react with steam by contact with a solid phosphoric acid catalyst, thereby directly synthesizing ethanol.

Isopropanol is also mostly produced either by direct hydration of propylene obtained from petroleum or by oxidation of propylene with sulfuric acid.

As described above, butanol, ethanol, and isopropanol have been mostly produced by chemical synthesis, and studies on these bio-alcohols have received increasing attention worldwide due to oil price rises and environmental concerns. However, efficient simultaneous production of biobutanol, ethanol, and isopropanol has not yet reported.

Production of butanol and ethanol by fermentation is possible in some *Clostridium* strains, including *Clostridium beijerinkii* NRRL B592, *C. beijerinkii* NRRL B593, *C. beijerinkii* IAM 19015, *C. beijerinkii* ATCC 14823, *C. beijerinkii* NCIMB 9581 and the like (Shaheen et al., *J. Mol. Microbiol. Biotechnol.*, 2: 115, 2000). However, the total concentration of organic solvents, including butanol, ethanol, and isopropanol, which are produced by these strains, is as very low as 11.3 g/l (*C. beijerinkii* NRRL B592), 11.5 g/l (*C. beijerinkii* NRRL B593), 12.0 g/l (*C. beijerinkii* IAM 19015), 4.4 g/l (*C. beijerinkii* ATCC 14823), and 3.3 g/l (*C. beijerinkii* NCIMB 9581), indicating that these organic solvents cannot be used for industrial purposes.

Meanwhile, *C. acetobutylicum* ATCC 824 and the like which produce butanol, isopropanol, and ethanol also produce acetone which is regarded as a byproduct in the production of mixed alcohols, increases the separation and purification costs and reduces the carbon yield. Previous studies on reducing the production of acetone reported that: 1) overexpression of aad (alcohol/aldehyde dehydrogenase) resulted in a decrease in the ratio of the production of acetone to the production of butanol and ethanol as compared to the wild type strain (Nair et al., *J. Bacteriol.*, 176:871, 1994); 2) inactivation of the buk gene resulted in an increase in the production of butanol to 16.7 g/l, thus reducing the ratio of the production of acetone (Harris et al., *Biotechnol. Bioeng.*, 67:1, 2000); and 3) the use of *C. beijerinckii* BA101, a mutant strain caused by random mutation, increased the production of butanol to 18.6 g/l, thus reducing the ratio of the production of acetone (Ezeji et al., *Appl. Microbiol. Biotechnol.*, 63:653, 2004). However, the above three examples all have a disadvantage in that the concentration of the byproduct acetone is not substantially reduced. In an attempt to produce ethanol and butanol while reducing or blocking the production of acetone, there was proposed the use of a recombinant mutant microorganism obtained by introducing aad (Nair et al., *J. Bacteriol.*, 176:5843, 1994) or aad-ctfAB (PCT/KR2008/007577) into a *Clostridium acetobutylicum* mutant strain which lacks adc (acetoacetic acid decarboxylase-encoding gene) (Jiang et al., *Metab. Eng.* doi:10.1016/j.ymben.2009.06.002, 2009), ctfA (CoA transferase A-encoding gene) and ctfB (CoA transferase B-encoding gene) (WO2008052596, and WO2008052973) and is defective in the activities of both aad (alcohol/aldehyde dehydrogenase) and ctfAB (CoA transferase AB-encoding gene). However, the recombinant mutant organism has a disadvantage in that the final concentration of a butanol/ethanol mixture is as low as 6-16.3 g/l, indicating that it cannot be used for industrial purposes. In addition, there is an example in which isopropanol was produced using a recombinant strain obtained by introducing the acetone-producing pathway and isopropanol-producing pathway of *Clostridium* into *E. coli* (Liao et al., *Appl. Environ. Microbiol.* 73:7814, 2007; US2008/0293125). Also, in this case, there are problems in that the alcohol concentration is as very low as 5 g/l and the byproduct acetone is also produced at a concentration of about 3.5 g/l.

Thus, in the art, there is an urgent need to develop microorganisms that highly efficiently produce butanol, ethanol, isopropanol, or mixtures thereof, which can be used directly as fuels, without producing byproducts such as acetone.

Accordingly, the present inventors have made extensive efforts to develop microorganisms that produce butanol or mixed alcohols with high efficiency without producing byproducts such as acetone, and as a result, have found that a recombinant mutant microorganism prepared by amplifying or introducing genes, which encode enzymes involved in producing butanol from butyryl-CoA or butylaldehyde and in producing isopropanol from acetone, in microorganisms of the genus *Clostridium*, produces a high concentration of butanol or mixed alcohols comprising butanol, ethanol, and isopropanol while producing little or no acetone as a byproduct, and have also found that a recombinant mutant microorganism prepared by treating a host microorganism, having the ability to produce butanol and ethanol, with a mutagen, to prepare a mutant microorganism, and then introducing a gene, which encodes an enzyme involved in isopropanol production, produces high concentrations of butanol, ethanol, and isopropanol while producing little or no acetone as a byproduct, thereby completing the present invention.

DISCLOSURE OF INVENTION

Accordingly, the present invention has been made in order to solve the above-mentioned problems occurring in the prior art, and it is an object of the present invention to provide a method for preparing recombinant mutant microorganisms having an increased ability to produce butanol or mixed alcohols, and recombinant mutant microorganisms prepared thereby.

Another object of the present invention is to provide a method of producing high concentrations of butanol or mixed alcohols comprising butanol, ethanol, isopropanol and the like without producing byproducts.

Still another object of the present invention is to provide recombinant mutant microorganisms having an increased ability to produce butanol, ethanol, and isopropanol, and a preparation method thereof.

Yet another object of the present invention is to provide a method of producing high concentrations of butanol, ethanol, and isopropanol without producing the byproduct acetone.

To achieve the above objects, the present invention provides a method of preparing a recombinant mutant microorganism having an increased ability to produce butanol or mixed alcohols and a reduced ability to produce acetone, the method comprising amplifying or introducing genes, which encode enzymes involved in producing butanol from butyryl-CoA or butylaldehyde and in producing isopropanol from acetone, in a host microorganism.

The present invention also provides a method of preparing a recombinant mutant microorganism having an increased ability to produce (A) butanol or (B) mixed alcohols comprising butanol and isopropanol, the method comprising amplifying or introducing a primary/secondary alcohol dehydrogenase-encoding gene (adhI) and an electron-transfer protein-encoding gene (hydG) in a microorganism of the genus *Clostridium*.

The present invention also provides a method for preparing a recombinant mutant microorganism having an increased ability to produce (A) butanol or (B) mixed alcohols comprising butanol and isopropanol, the method comprising amplifying or introducing a primary/secondary dehydrogenase-encoding gene (adhI), an electron-transfer protein-encoding gene (hydG), an acetoacetate decarboxylase-encoding gene (adc) and a CoA transferase-encoding gene (ctfA, ctfB) in a microorganism of the genus *Clostridium*.

The present invention also provides a recombinant mutant microorganism having an increased ability to produce butanol or mixed alcohols, wherein genes that encode enzymes involved in producing butanol from butyryl-CoA or butylaldehyde and in producing isopropanol from acetone were amplified or introduced in a host microorganism.

The present invention also provides a recombinant mutant microorganism having an increased ability to produce (A) butanol or (B) mixed alcohols comprising butanol and isopropanol, wherein a primary/secondary alcohol dehydrogenase-encoding gene (adhI) and an electron-transfer protein-encoding gene (hydG) were amplified or introduced in a microorganism of the genus *Clostridium*.

The present invention also provides a recombinant mutant microorganism having an increased ability to produce (A) butanol or (B) mixed alcohols comprising butanol and isopropanol, wherein a primary/secondary alcohol dehydrogenase-encoding gene (adhI), an electron-transfer protein-encoding gene (hydG), an acetoacetate decarboxylase-encoding gene (adc) and a CoA transferase-encoding gene (ctfA, ctfB) were amplified or introduced in a microorganism of the genus *Clostridium*.

The present invention also provides a method for producing butanol or mixed alcohols, the method comprising: culturing said recombinant mutant microorganism; and then recovering butanol or mixed alcohols from a culture medium used in the culture of the microorganism.

In addition, the present invention provides a method of preparing a mutant microorganism having an increased ability to produce butanol and ethanol, the method comprising preparing a mutant microorganism from a host microorganism having an ability to produce butanol and ethanol, wherein the mutant microorganism has an increased ability to produce butanol and ethanol, compared to the host microorganism, and the concentration or kind of one or more metabolites thereof, selected from the group consisting of acetone, acetic acid, butyric acid, lactic acid, acetoin, carbon dioxide, hydrogen and a $C_{2-10}$ straight or branched-chain alcohol, was changed compared to that of the host microorganism.

The present invention also provides a method for preparing a recombinant mutant microorganism having an increased ability to produce butanol, ethanol, and isopropanol, the method comprising: preparing a mutant microorganism from a host microorganism having the ability to produce butanol and ethanol, wherein the mutant microorganism has an increased ability to produce butanol and ethanol, compared to the host microorganism, and the concentration or kind of one or more metabolites thereof, selected from the group consisting of acetone, acetic acid, butyric acid, lactic acid, acetoin, carbon dioxide, hydrogen and a $C_{2-10}$ straight or branched-chain alcohol, was changed compared to that of the host microorganism; and amplifying or introducing a gene, which encodes an enzyme involved in isopropanol biosynthesis, in the mutant microorganism.

The present invention also a method for preparing a recombinant mutant microorganism having an increased ability to produce butanol, ethanol, and isopropanol, the method comprising: treating a microorganism of the genus *Clostridium*, which has the ability to produce butanol and ethanol, with N-methyl-N'-nitro-N-nitrosoguanidine (NTG or MNNG), to prepare a mutant microorganism having an increased ability to produce butanol and ethanol; and amplifying or introducing a primary/secondary alcohol dehydrogenase-encoding gene (adhI) and an electron-transfer protein-encoding gene (hydG) in the mutant microorganism.

The present invention also provides a method for preparing a recombinant mutant microorganism having an increased ability to produce butanol, ethanol, and isopropanol, the method comprising: treating a microorganism of the genus *Clostridium*, which has the ability to produce butanol and ethanol, with N-methyl-N'-nitro-N-nitrosoguanidine (NTG or MNNG), to prepare a mutant strain having an increased ability to produce butanol and ethanol; and amplifying or introducing a primary/secondary alcohol dehydrogenase-encoding gene (adhI), an electron-transfer protein-encoding gene (hydG), an acetoacetate decarboxylase-encoding gene (adc) and a CoA transferase-encoding gene (ctfA, ctfB) in the mutant microorganism.

The present invention also provides a mutant microorganism having an increased ability to produce butanol and ethanol, prepared by said method for preparing the mutant microorganism.

The present invention also provides a recombinant mutant microorganism having an increased ability to produce butanol, ethanol, and isopropanol, prepared by said method for preparing the recombinant mutant microorganism.

The present invention also provides a method for producing butanol, ethanol, and isopropanol, the method comprising culturing said recombinant mutant microorganism, and recovering butanol, ethanol, and isopropanol from a culture medium used in the culture of the microorganism.

The present invention also provides a method for producing butanol and ethanol, the method comprising culturing said mutant microorganism, and recovering butanol and ethanol from a culture medium used in the culture of the microorganism.

The present invention also provides a method for producing butanol and ethanol, the method comprising culturing said recombinant mutant microorganism, and recovering butanol from a culture medium used in the culture of the microorganism.

The present invention also provides a method for producing butanol, the method comprising culturing said recombinant mutant microorganism, and recovering butanol from a culture medium used in the culture of the microorganism.

Other features and embodiments of the present invention will be more apparent from the following detailed descriptions and the appended claims

BEST MODE FOR CARRYING OUT THE INVENTION

Figure 1:
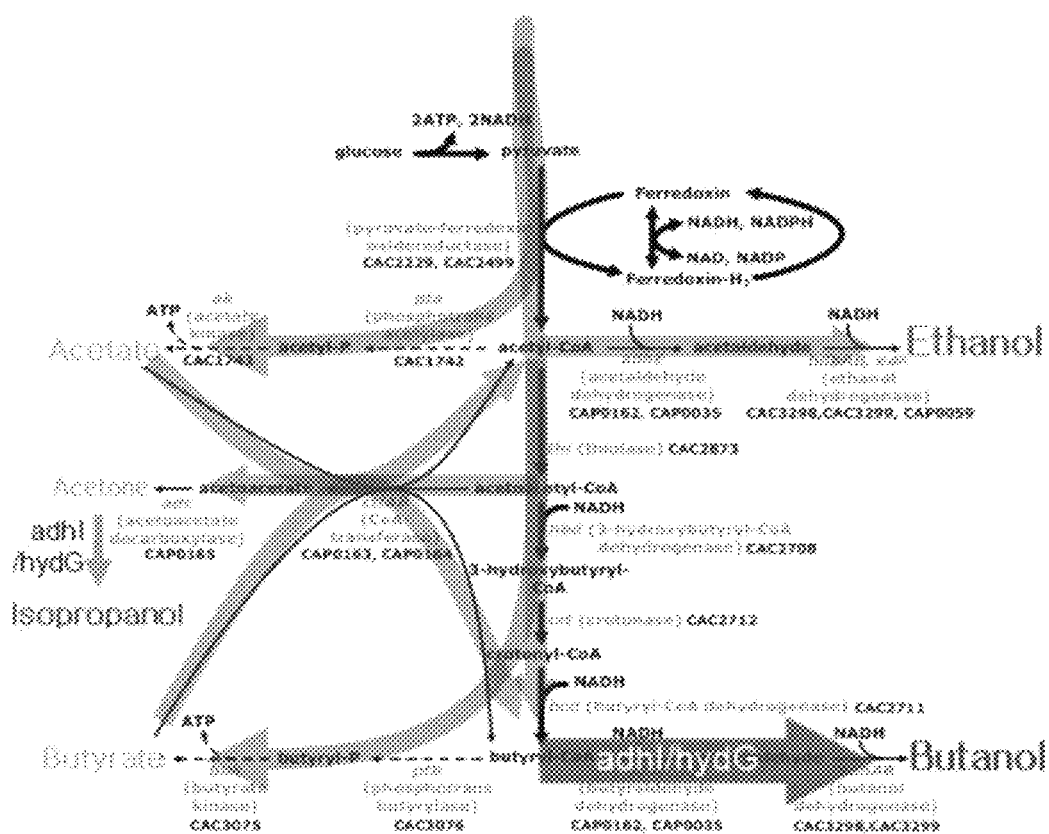
FIG. 1 shows the major metabolic pathways of a mutant *Clostridium* strain, which produce butanol, ethanol, acetone, acetic acid and butyric acid.
Figure 2:
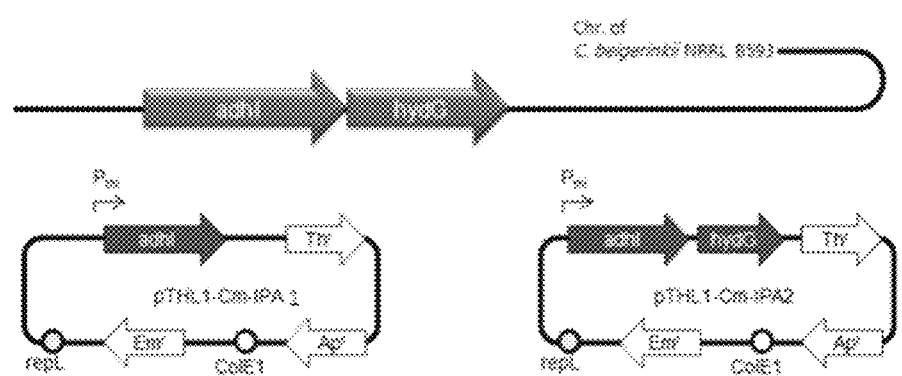
FIG. 2 shows genetic maps of the recombinant vectors pTHL1-Cm-IPA1 and pTHL1-Cm-IPA2 comprising adhI and/or hydG.

In the present invention, a recombinant mutant microorganism was prepared in which genes, which encode enzymes involved in producing butanol from butyryl-CoA or butylaldehyde and in producing isopropanol from acetone, were amplified or introduced, and whether the recombinant mutant microorganism could produce butanol or ethanol with high yield without producing little or no acetone as a byproduct was examined.

In one Example of the present invention, a primary/secondary dehydrogenase-encoding gene and an electron-transfer protein-encoding gene, which are derived from *Clostridium beijerinckii* NRRL B593 and convert either acetone to isopropanol or butyryl-CoA and butyraldehyde to butanol, were cloned, and the genes were introduced into a host microorganism having genes, which encode enzymes involved in the biosynthetic pathway to primary/secondary acyl CoA or primary/secondary aldehyde, and/or an acetone biosynthetic pathway, thereby constructing a recombinant mutant microorganism. In addition, the constructed recombinant mutant microorganism was confirmed to produce a high yield of butanol, ethanol, isopropanol, or mixtures thereof without producing little or no acetone as a byproduct.

In the present invention, "having a specific metabolic pathway" means that not only a strain originally has the metabolic pathway, but also a foreign gene is introduced by techniques, including recombination and genome shuffling.

Thus, in one aspect, the present invention is directed to a method of preparing a recombinant mutant microorganism having an increased ability to produce butanol or mixed alcohols and a reduced ability to produce acetone, the method comprising amplifying or introducing genes, which encode enzymes involved in producing butanol from butyryl-CoA or butylaldehyde and in producing isopropanol from acetone, in a host microorganism, and a recombinant mutant microorganism having an increased ability to produce butanol or mixed alcohols and a reduced ability to produce acetone, prepared by said method.

In the present invention, the genes, which encode enzymes involved in producing butanol from butyryl-CoA or butylaldehyde and in producing isopropanol from acetone, are a primary/secondary alcohol dehydrogenase-encoding gene and an electron-transfer protein-encoding gene. That is, the primary/secondary alcohol dehydrogenase-encoding gene and the electron-transfer protein-encoding gene all function to be involved in the production of butanol from butyryl-CoA or butylaldehyde and in the production of isopropanol from acetone.

In the present invention, the gene that encodes primary/secondary alcohol dehydrogenase may be adhI, and the gene that encodes the electron-transfer protein may be hydG. In the present invention, said adhI and hydG genes are exemplified by those derived from *Clostridium beijerinckii* NRRL B593, but even genes derived from other microorganisms may be used without limitation, so long as they are expressed in a host cell introduced to exhibit the same activities.

As used herein, the term "biosynthetic pathway" is meant to include pathways in which a compound of interest is synthesized from a specific metabolite in a cell, without being limited only to pathways in which the compound of interest is synthesized from carbons provided through the relevant process (glycolysis).

In the present invention, the host microorganism may comprise one or more metabolic pathways selected from the group consisting of: (A) an acetyl-CoA biosynthetic pathway; (B) a butyryl-CoA biosynthetic pathway; (C) an acetone biosynthetic pathway; (D) an ethanol biosynthetic pathway; (E) a butanol biosynthetic pathway; (F) an isobutanol biosynthetic pathway; (G) a propanol biosynthetic pathway; and (H) an isopropanol biosynthetic pathway.

In the present invention, a microorganism having the above-described metabolic pathway may be used as a host microorganism without limitation, but a microorganism of the genus *Clostridium* is preferably used.

Examples of the microorganisms of the genus *Clostridium* may include *Clostridium acetobutylicum, Clostridium beijerinckii, Clostridium saccharobutylicum, Clostridium saccharoperbutylacetonicum, Clostridium perfringens, Clostridium tetani, Clostridium difficile, Clostridium butyricum, Clostridium butylicum, Clostridium kluyveri, Clostridium tyrobutylicum, Clostridium tyrobutyricum,* and the like.

In addition, preferably, the host microorganism is one in which one or more biosynthetic pathways selected from the group consisting of: (A) an acetic acid biosynthetic pathway; (B) a butyric acid biosynthetic pathway; (C) a lactic acid biosynthetic pathway; (D) an acetoin biosynthetic pathway; and (E) a hydrogen biosynthetic pathway were completely blocked or regulated.

As used herein, the term "regulating" is meant to include evoluting or mutating one or more of enzymes present in a biosynthetic pathway or regulating the expression of enzymes present in a biosynthetic pathway.

Examples of the host microorganism include a *Clostridium acetobutylicum* mutant M5 strain lacking a megaplasmid (carrying 127 genes, including an acetoacetic acid decarboxylase-encoding gene, a CoA transferase-encoding gene, and an alcohol/aldehyde dehydrogenase-encoding gene), used in one example of the present invention; a *Clostridium acetobutylicum* ATCC 824 strain; a buk mutant lacking the butyrate kinase-encoding gene of *Clostridium acetobutylicum*; an eutD or pta mutant lacking the phosphotransacetylase-encoding gene of *Clostridium acetobutylicum*; and a BKM19 strain that produces high concentrations of butanol and ethanol by evolution.

In the present invention, the mixed alcohols comprise butanol and isopropanol, and may further comprise $C_{2-10}$ straight or branched-chain alcohols, including ethanol, isobutanol, propanol, hexanol, heptanol, octanol, nonanol, decanol, tert-butanol, 1-pentanol, 2-pentanol, 3-pentanol, 2-methyl-1-butanol, 3-methyl-1-butanol, 2-methyl-2-butanol, and the like.

In another aspect, the present invention is also directed to a method of preparing a recombinant mutant microorganism having an increased ability to produce (A) butanol or (B) mixed alcohols comprising butanol and isopropanol, the method comprising amplifying or introducing a primary/secondary alcohol dehydrogenase-encoding gene (adhI) and an electron-transfer protein-encoding gene (hydG) in a microorganism of the genus *Clostridium*, and a recombinant mutant microorganism having an increased ability to produce (A) butanol or (B) mixed alcohols comprising butanol and isopropanol, prepared by said method.

In another example of the present invention, a recombinant microorganism was constructed in which a primary/secondary alcohol dehydrogenase-encoding gene (adhI) and an electron-transfer protein-encoding gene (hydG), as well as an acetoacetate decarboxylase-encoding gene (adc) and a CoA transferase-encoding gene (ctfA, ctfB), which encode enzymes involved in acetone biosynthesis, were amplified or introduced in a microorganism of the genus *Clostridium* in order to increase the metabolic flux into acetone. The recombinant microorganism was confirmed to have an increased ability to produce butanol and mixed alcohols and a reduced ability to produce acetone.

Thus, in still another aspect, the present invention is directed to a method of preparing a recombinant mutant microorganism having an increased ability to produce (A) butanol or mixed alcohols and a reduced ability to produce (B) acetone, the method comprising amplifying or introducing genes that encode enzymes involved in producing butanol from butyryl-CoA or butylaldehyde and in producing isopropanol from acetone, and genes that encode enzymes involved in acetone biosynthesis, in a host microorganism, and a recombinant mutant microorganism having an increased ability to produce butanol or mixed alcohols and a reduced ability to produce acetone, prepared by said method.

The genes that encode enzymes involved in acetone biosynthesis may include an acetoacetate decarboxylase-encoding gene (adc) and a CoA transferase-encoding gene (ctfA, ctfB).

Further, in yet another aspect, the present invention is directed to a method of preparing a recombinant mutant microorganism having an reduced ability to produce acetone, the method comprising amplifying or introducing a primary/secondary alcohol dehydrogenase-encoding gene (adhI) and an electron-transfer protein-encoding gene (hydG) in a microorganism that produces acetone as a final product, and a recombinant mutant microorganism having an reduced ability to produce acetone.

Meanwhile, in another example of the present invention, the recombinant mutant microorganisms M5 (pTHL1-Cm-IPA1), M5 (pTHL1-Cm-IPA2), PTA (pTHL1-Cm-IPA1), PTA (pTHL1-Cm-IPA2), BKM19 (pTHL1-Cm-IPA1) and BKM19 (pTHL1-Cm-IPA2) were prepared by introducing a recombinant vector (pTHL1-Cm-IPA1 or pTHL1-Cm-IPA2) containing adhI or adhI-hydG into the host microorganisms, and were then cultured. As a result, it was found that the recombinant mutant microorganisms produced high concentrations of butanol or mixed alcohols comprising butanol and isopropanol without producing little or no acetone.

Thus, in a further aspect, the present invention is directed to a method for producing butanol or mixed alcohols, the method comprising: culturing a recombinant mutant microorganism wherein genes that encode enzymes involved in producing butanol from butyryl-CoA or butylaldehyde and in producing isopropanol from acetone were amplified or introduced in a host microorganism; and then recovering butanol or mixed alcohols from a culture medium used in the culture of the microorganism.

In a still further aspect, the present invention is directed to a method for producing butanol or mixed alcohols, the method comprising culturing a recombinant mutant microorganism wherein a primary/secondary alcohol dehydrogenase-encoding gene (adhI) and an electron-transfer protein-encoding gene (hydG) were amplified or introduced in a microorganism of the genus *Clostridium*, and then recovering (A) butanol or (B) mixed alcohols comprising butanol and isopropanol from a culture medium used in the culture of the microorganism.

In the present invention, the genes that encode enzymes involved in producing butanol from butyryl-CoA or butylaldehyde and in producing isopropanol from acetone, the electron-transfer protein-encoding gene, the host microorganism, and the like are the same as those described in the above.

In the present invention, the culture of the recombinant mutant microorganism and the recovery of single alcohols and mixed alcohols may be performed using a conventional culture method and alcohol separation and purification method known in the fermentation industry. In addition, the recovery of (A) butanol or (B) mixed alcohols comprising butanol and isopropanol is generally carried out after completion of the culture, but may also be carried out during the culture using a gas-stripping method (Thaddeus et al., *Bioprocess Biosyst. Eng.*, 27:207, 2005) in order to increase productivity. In other words, carrying out the culture while recovering (A) butanol or (B) mixed alcohols comprising butanol and isopropanol, produced during the culture, also falls within the scope of the present invention.

Meanwhile, in the present invention, a recombinant mutant microorganism was prepared by treating a host microorganism, having the ability to produce butanol and ethanol, treated with a mutagen, to prepare a mutant microorganism having an increased ability to produce butanol and ethanol, and then a gene, which encodes an enzyme involved in isopropanol biosynthesis, in the mutant microorganism, and whether the prepared recombinant mutant microorganism can produce high yields of butanol, ethanol, and isopropanol without producing little or no acetone was examined.

In another example of the present invention, a *Clostridium acetobutylicum* strain having the ability to produce butanol and ethanol was treated with a mutagen (NTG or MNNG), thereby preparing a mutant microorganism in which the concentration of acetic acid, butyric acid, butanol, acetone or ethanol was changed. Then, a recombinant mutant microorganism was constructing by amplifying or introducing a primary/secondary alcohol dehydrogenase-encoding gene (adhI) and an electron-transfer protein-encoding gene (hydG) in the mutant microorganism. In addition, it was confirmed that the constructed recombinant mutant microorganism produce high yields of butanol, ethanol, and isopropanol without producing little or no acetone as a byproduct.

Thus, in one aspect, the present invention is directed to a method of preparing a mutant microorganism having an increased ability to produce butanol and ethanol, the method comprising preparing a mutant microorganism from a host microorganism having an ability to produce butanol and ethanol, wherein the mutant microorganism has an increased ability to produce butanol and ethanol, compared to the host microorganism, and the concentration or kind of one or more metabolites thereof, selected from the group consisting of acetone, acetic acid, butyric acid, lactic acid, acetoin, carbon dioxide, hydrogen and a $C_{2-10}$ straight or branched-chain alcohol, was changed compared to that of the host microorganism.

In addition, in another aspect, the present invention is directed to a method for preparing a recombinant mutant microorganism having an increased ability to produce butanol, ethanol, and isopropanol, the method comprising: preparing a mutant microorganism from a host microorganism having the ability to produce butanol and ethanol, wherein the mutant microorganism has an increased ability to produce butanol and ethanol, compared to the host microorganism, and the concentration or kind of one or more metabolites thereof, selected from the group consisting of acetone, acetic acid, butyric acid, lactic acid, acetoin, carbon dioxide, hydrogen and a $C_{2-10}$ straight or branched-chain alcohol, was changed compared to that of the host microorganism; and amplifying or introducing a gene, which encodes an enzyme involved in isopropanol biosynthesis, in the mutant microorganism, and is also directed to a recombinant mutant microorganism having an increased ability to produce butanol, ethanol, and isopropanol, prepared by said method.

In the present invention, the host microorganism having the ability to produce butanol and ethanol may be one in which one or more biosynthetic pathways selected from the group consisting of (a) an acetyl-CoA biosynthetic pathway, (b) a butyryl-CoA biosynthetic pathway, (c) an acetone biosynthetic pathway, (d) an ethanol biosynthetic pathway, (e) a butanol biosynthetic pathway, (f) an acetic biosynthetic pathway, and (g) a butyric acid biosynthetic pathway were introduced, deleted or regulated.

In the present invention, "having the ability to produce butanol and ethanol" means that not only a strain originally has the ability to produce butanol and ethanol, but also a foreign gene is introduced in the strain by techniques, including recombination and genome shuffling.

The host microorganism may be derived from the genus *Clostridium*, but is not limited thereto, so long as it has a pathway capable of biosynthesizing one or more selected from the group consisting of butanol, ethanol and acetone.

In the present invention, the biosynthetic pathway that is blocked or regulated by recombination may be an acetic acid or butyric acid biosynthetic pathway, but is not limited thereto, so long as one or more of an acetic acid-producing pathway and a butyric acid-producing pathway are blocked or regulated.

In the present invention, the mutant microorganism can be prepared by treating a host microorganism with a mutagen. The mutagen may be used without limitation, so long as it can mutate microorganisms. Examples of the mutagen include proflavine, acridine orange, N-methyl-N'-nitro-N-nitrosoguanidine (NTG or MNNG), 4-nitroqyinoline 1-oxide (4-NQO), nitrite ($HNO_2$), hydroxylamine ($NH_2OH$), dimethylsulfate (DMS), diethylsulfate (DES), ethyl ethanesulfonate (EES), methyl methanesulfonate (MMS), ethyl methanesulfonate (EMS) and the like.

The mutant microorganism prepared by treatment with the mutagen may be one in which the concentration or kind of one or more metabolites acetone, acetic acid, butyric acid, lactic acid, acetoin, carbon dioxide, hydrogen and a $C_{2-10}$ straight or branched-chain alcohol was changed compared to that of the host microorganism. Examples of the $C_{2-10}$ straight or branched-chain alcohol include ethanol, butanol, isopropanol, hexanol, heptanol, octanol, nonanol, decanol, isobutanol, propanol, tert-butanol, 1-pentanol, 2-pentanol, 3-pentanol, 2-methyl-1-butanol, 3-methyl-1-butanol, 2-methyl-2-butanol and the like.

In the present invention, among mutant microorganisms in which the concentration or kind of various metabolites was changed, a mutant microorganism having an increased ability to produce butanol and ethanol is preferably used.

The present invention is characterized in that genes which encode involved in isopropanol biosynthesis, that is, a primary/secondary alcohol dehydrogenase-encoding gene and an electron-transfer protein-encoding gene, are introduced into the mutant microorganism in order to remove acetone from the metabolites of the mutant microorganism. The primary/secondary alcohol dehydrogenase-encoding gene and the electron-transfer protein-encoding gene all function to be involved in the production of isopropanol from acetone.

The primary/secondary alcohol dehydrogenase-encoding gene may be adhI, and the electron-transfer protein-encoding gene may be hydG. In the present invention, the adhI and hydG genes are exemplified by only those derived from *Clostridium beijerinkii* NRRL B593, but even genes derived from other microorganisms may be used without limitation, so long as they are expressed in a host cell to exhibit the same activities.

Thus, in still another aspect, the present invention is directed to a method for preparing a recombinant mutant microorganism having an increased ability to produce butanol, ethanol, and isopropanol, the method comprising: treating a microorganism of the genus *Clostridium*, which has the ability to produce butanol and ethanol, with N-methyl-N'-nitro-N-nitrosoguanidine (NTG or MNNG), to prepare a mutant microorganism having an increased ability to produce butanol and ethanol; and amplifying or introducing a primary/secondary alcohol dehydrogenase-encoding gene (adhI) and an electron-transfer protein-encoding gene (hydG) in the mutant microorganism, and is also directed to a recombinant mutant microorganism having an increased ability to produce butanol, ethanol, and isopropanol, prepared by said method.

Examples of the mutant microorganism having an increased ability to produce butanol and ethanol, prepared by the preparation method of the present invention, include *Clostridium acetobutylicum* BKM19 (KCTC 11555BP), and examples of the recombinant mutant microorganism prepared by the method of the present invention include *Clostridium acetobutylicum* BKM19 (pTHL1-Cm-IPA1), *Clostridium acetobutylicum* BKM19 (pTHL1-Cm-IPA2) and the like.

In another example of the present invention, a recombinant microorganism was constructed in which a primary/secondary alcohol dehydrogenase-encoding gene (adhI) and an electron-transfer protein-encoding gene (hydG), as well as an acetoacetate decarboxylase-encoding gene (adc) and a CoA transferase-encoding gene (ctfA, ctfB), which encode enzymes involved in acetone biosynthesis, were amplified or introduced in a mutant microorganism #104 (*Clostridium acetobutylicum* BKM19) having an increased ability to produce ethanol, in order to increase the metabolic flux into acetone. In addition, the constructed recombinant microorganism was confirmed to have an increased ability to produce butanol or mixed alcohols and a reduced ability to produce acetone.

Thus, in yet another aspect, the present invention is directed to a method for preparing a recombinant mutant microorganism having an increased ability to produce butanol, ethanol, and isopropanol, the method comprising: preparing a mutant microorganism from a host microorganism having the ability to produce butanol and ethanol, wherein the mutant microorganism has an increased ability to produce butanol and ethanol, compared to the host microorganism, and the concentration or kind of one or more metabolites thereof, selected from the group consisting of acetone, acetic acid, butyric acid, lactic acid, acetoin, carbon dioxide, hydrogen and a $C_{2-10}$ straight or branched-chain alcohol, was changed compared to that of the host microorganism; and amplifying or introducing a gene that encodes an enzyme involved in isopropanol biosynthesis and a gene that encodes an enzyme involved in acetone biosynthesis, in the mutant microorganism.

The gene that encodes an enzyme involved in acetone biosynthesis may include an acetoacetate decarboxylase-encoding gene (adc) or a CoA transferase-encoding gene (ctfA, ctfB).

Examples of the recombinant microorganism in which the primary/secondary alcohol dehydrogenase-encoding gene (adhI) and the electron-transfer protein-encoding gene (hydG), as well as the genes that encode enzymes involved in acetone biosynthesis, were amplified or introduced in the mutant microorganism, include *Clostridium acetobutylicum* BKM19 (pIPA3), *Clostridium acetobutylicum* BKM19 (pIPA4) and the like.

In the present invention, the recombinant mutant microorganism produces mixed alcohols (including butanol) at a concentration of 16-40 g/l and produces ethanol and butanol at an ethanol:butanol ratio of 1:6 to 2:1. In addition, the recombinant mutant microorganism produces acetone at a concentration of 0.01-4 g/l, and preferably 0.1-1 g/l.

In a further aspect, the present invention is directed to a method for producing butanol, ethanol, and isopropanol, the method comprising culturing said recombinant mutant microorganism, and recovering butanol, ethanol, and isopropanol from a culture medium used in the culture of the microorganism.

Said butanol, ethanol, and isopropanol may be recovered separately or as mixed alcohols.

Thus, in a still further aspect, the present invention is directed to a method for producing butanol and ethanol, the method comprising culturing said recombinant mutant microorganism, and recovering butanol and ethanol from a culture medium used in the culture of the microorganism, and to a method for producing butanol, the method comprising culturing said recombinant mutant microorganism, and recovering butanol from a culture medium used in the culture of the microorganism.

In the present invention, the culture of recombinant microorganisms and the recovery of pure alcohols and mixed alcohols may be performed using a conventional culture methods and alcohol separation and purification method known in the fermentation industry. In addition, the recovery of alcohols is generally carried out after completion of the culture of microorganisms, but alcohols may also be recovered using a gas-stripping method or the like during culture in order to increase productivity. In other words, carrying out the culture of microorganisms while recovering butanol and ethanol and/or isopropanol, produced during the culture, also falls within the scope of the present invention.

EXAMPLES

Hereinafter, the present invention will be described in further detail with reference to examples. It will be obvious to a person having ordinary skill in the art that these examples are illustrative purposes only and are not to be construed to limit the scope of the present invention.

In the following examples, a host strain in which a gene according to the present invention would be expressed was particularly exemplified by only specific *Clostridium acetobutylicum* strains. However, it will be obvious to a person skilled in the art that, even when other microorganisms of the genus *Clostridium* or microorganisms of other genera are used, the same gene as described in the examples may be introduced into a host strain having genes, which encode enzymes involved in the biosynthetic pathway to primary/secondary acyl CoA or primary/secondary aldehyde, and/or an acetone producing pathway, and the resulting strain may be used to produce butanol or mixed alcohols comprising butanol and isopropanol.

Furthermore, in the following examples, a host strain according to the present invention was exemplified by only specific *Clostridium acetobutylicum* strains. However, it will be obvious to a person skilled in the art that other microorganisms of the genus *Clostridium* or microorganisms of other genera are used may be used without limitation, so long as they have a pathway capable of biosynthesizing one or more selected from the group consisting of butanol, ethanol and acetone.

In addition, in the following examples, only the production of butanol, the production of butanol and isopropanol and the production of butanol, ethanol, and isopropanol were illustrated; however, the production of mixed alcohols comprising other alcohols will also be obvious to a person skilled in the art.

Example 1

Construction of pTHL1-Cm Vector

A shuttle vector for foreign protein expression comprising the thiolase promoter and ribosome binding site (RBS) of *Clostridium acetobutylicum* was constructed in the following manner. It is known that thiolase can continuously and stably express a gene without being greatly influenced by the cell growth cycle (Tummala et al., Appl. Environ. Microbiol., 65:3793~3799, 1999). Thus, in this Example, the promoter at the top of thiolase (NCBI GeneID: 1119056) was cloned and inserted into pIMP-H1del. pIMP-H1del is a shuttle vector, which has pIMP1 as a template and is obtained by removing a HindIII site at position 3408 of pIMP1 having two HindIII restriction enzyme while leaving the restriction enzyme site at position 743 of pIMP1. The thiolase promoter was amplified by PCR using the total DNA of the *Clostridium acetobutylicum* ATCC 824 strain with primers of SEQ ID NOS: 1 and 2. The amplified thiolase promoter fragment was purified and recovered, after which it was treated with HindIII and PstI restriction enzymes and ligated with the pIMP-H1del shuttle vector treated with the same restriction enzymes, thereby constructing a pTHL1 vector.

```
[SEQ ID NOS: 1]:
5'-GGCCCCAAGCTTAGAATGAAGTTTCTTATGCACAAG-3'

[SEQ ID NOS: 2]:
5'-AAACTGCAGTCTAACTAACCTCCTAAATTTTGATAC-3'
```

In addition, a chloramphenicol resistance gene was amplified by PCR using pSOS95-Cm as a template with primers of SEQ ID NOS: 3 and 4. The amplified gene chloramphenicol resistance fragment was purified and recovered, after which it was treated with a HindIII restriction enzyme and ligated with the pTHL1 shuttle vector treated with the same restriction enzyme, thereby constructing a pTHL1-Cm vector. pSOS95-Cm can be constructed by cloning the thiolase promoter of the ATCC 824 strain into pSOS95 (Nair and Papoutsakis, J. Bacteriol., 176:5843-5846, 1994) and cloning a chloramphenicol/thiamphenicol resistance gene downstream of the promoter.

```
[SEQ ID NOS: 3]:
5'-CCAAGCTTCGACTTTTTAACAAAATATATTG-3'

[SEQ ID NOS: 4]:
5'-CCAAGCTTGACATTAAAAAAATAAGAGTTACC-3'
```

Example 2

Construction of Expression Vectors pTHL1-Cm-IPA1 and pTHL1-Cm-IPA2 which Express Primary/Secondary Alcohol Dehydrogenase and/or Electron-Transfer Protein In order to enable primary/secondary alcohol dehydrogenase and/or electron-transfer protein to be expressed in *Clostridium acetobutylicum*, genes that encode primary/secondary alcohol dehydrogenase and/or electron-transfer protein were cloned into the pTHL1-Cm vector constructed in Example 1.

PCR was performed using as a template the total DNA of *Clostridium beijerinkii* NRRL B593 having genes, which encode primary/secondary alcohol dehydrogenase and electron-transfer protein, with a primer pair of SEQ ID NOS: 5 and 6 or a primer pair of SEQ ID NOS: 5 and 7, thereby amplifying adhI and adhI-hydG fragments, respectively.

```
[SEQ ID NOS: 5]:
5'-AAAACTGCAGATGAAAGGTTTTGCAATGCTA-3'

[SEQ ID NOS: 6]:
5'-CCCCCGGGGTGTATAATCCTCCATGATCTATTATG-3'

[SEQ ID NOS: 7]:
5'-CCCCCGGGGCCTTCTACACATTTAGGATTCTTAC-3'
```

The amplified adhI fragment was treated with PstI and AvaI restriction enzymes, after which it was ligated by T4 DNA ligase with the pTHL1-Cm vector treated with the same restriction enzymes, thereby preparing the recombinant plasmid pTHL1-Cm-IPA1. Meanwhile, the amplified adhI-hydG fragment was treated with PstI and AvaI restriction enzymes, after which it was ligated by T4 DNA ligase with the pTHL1-Cm vector treated with the pTHL1-Cm vector treated with the same restriction enzymes, thereby preparing the recombinant plasmid pTHL1-Cm-IPA2.

Example 3

Production of Butanol by Recombinant Mutant Microorganism

The *Clostridium acetobutylicum* M5 strain has a characteristic in that, because it lacks a megaplasmid (carrying genes, including an acetoacetic acid decarboxylase-encoding gene, a CoA transferase-encoding gene, and an alcohol/aldehyde dehydrogenase-encoding gene), it cannot produce butanol, ethanol and acetone. Each of the recombinant vectors pTHL1-Cm-IPA1 and pTHL1-Cm-IPA2 constructed in Example 2 was introduced into the *Clostridium acetobutylicum* M5 strain by electroporation, thereby constructing M5 (pTHL1-Cm-IPA1) and M5 (pTHL1-Cm-IPA2) strains.

First, each of the recombinant vectors constructed in Example 2 was introduced into *E. coli* TOP10 containing the *Bacillus subtilis* Phage Φ3T I methyltransferase expression vector pAN1 (Mermelstein et al., *Appl. Environ. Microbiol.*, 59:1077, 1993), thereby inducing the methylation of the vectors so as to make the vectors suitable for transformation into *Clostridium*. Each of the methylated vectors was separated and purified from the *E. coli* strain and introduced into the *Clostridium acetobutylicum* M5 strain lacking a megaplasmid (Cornillot et al., *J. Bacteriol.*, 179:5442, 1997), thereby preparing recombinant mutant microorganisms. In addition, pIMP1 used as the cloning vector was introduced into the *Clostridium acetobutylicum* M5 strain, thereby preparing a M5 (pIMP1) strain.

M5 competent cells for transformation were prepared in the following manner. First, the M5 strain was inoculated into 10 ml of CGM (Table 1), and then cultured until an O.D. of 0.6 was reached. Then, the strain was inoculated into 60 ml of 2×YTG medium (per liter, 16 g of bacto tryptone, 10 g yeast extract, 4 g of NaCl, and 5 g of glucose) at a concentration of 10% and cultured for 4-5 hours. The microbial cells were washed twice with transformation buffer (EPB, 15 ml of 270 mM sucrose, 110 µl of 686 mM $NaH_2PO_4$, pH 7.4), and then suspended in 2.4 ml of the same buffer. 600 µl of the M5 competent cells thus made were mixed with 25 µl of the recombinant plasmid DNA, and the mixture was loaded into a cuvette having a 4 mm electrode gap and then subjected to electric shock at 2.5 kV and 25 uF. Then, the cells were immediately suspended in 1 ml of 2×YTG medium and cultured at 37° C. for 3 hours, after which the cells were plated on a 2×YTG solid medium containing 40 µg/ml of erythromycin, and the transformants M5 (pTHL1-Cm-IPA1) and M5 (pTHL1-Cm-IPA2) were selected.

The recombinant mutant microorganisms M5 (pTHL1-Cm-IPA1) and M5 (pTHL1-Cm-IPA2) were cultured and their abilities to produce alcohols were evaluated. A 30-ml test tube containing 10 ml of CGM medium was sterilized, and then taken when it reached a temperature of 80° C. or higher. Then, the test tube was charged with nitrogen gas and cooled to room temperature in an anaerobic chamber. Then, 40 µg/ml of erythromycin was added thereto, and the recombinant mutant microorganisms were inoculated into the test tube and cultured at 37° C. under anaerobic conditions for 48 hours. After completion of the culture, the supernatant was collected and the concentrations of acetone, ethanol and butanol in the collected supernatant were measured by gas chromatography (Agillent 6890N GC System, Agilent Technologies Inc., CA, USA) equipped with a packed column (Supelco Carbopack™ B AW/6.6% PEG 20M, 2 m×2 mm ID, Bellefonte, Pa., USA).

TABLE 1

| Components | Contents (g/l) |
|---|---|
| Glucose | 80 |
| $K_2HPO_4 \cdot 3H_2O$ | 0.982 |
| $KH_2PO_4$ | 0.75 |
| $MgSO_4$ | 0.348 |
| $MnSO_4 \cdot H_2O$ | 0.01 |
| $FeSO_4 \cdot 7H_2O$ | 0.01 |
| $(NH_4)_2SO_4$ | 2 |
| NaCl | 1 |
| Asparagine | 2 |
| p-Aminobenzoic acid | 0.004 |
| Yeast extract | 5 |

As a result, in the control M5 (pTHL1-Cm) and the recombinant strain M5 (pTHL1-Cm-IPA1) that is the test group, no ethanol and butanol were produced, whereas in the recombinant strain M5 (pTHL1-Cm-IPA2), 6.5 g/l of butanol was produced. This suggests that the hydG gene plays an important role in the production of butanol.

Example 4

Production of Mixed Alcohols of Butanol and Isopropanol by Recombinant Mutant Microorganism 4-1: Construction of Vector Comprising Mutant loxP Site and Antibiotic Resistance Marker In the case of *Clostridium acetobutylicum*, an erythromycin resistance gene (hereinafter referred to as $Em^r$) is mainly used as an antibiotic resistance marker for a vector. For gene deletion by double crossover recombination, an additional antibiotic resistance marker is required to select a strain in which a double crossover occurred. Thus, pSOS95-Cm that expresses a chloramphenicol/thiamphenicol resistance marker (hereinafter referred to as $Th^r$) using the thiolase promoter of *Clostridium acetobutylicum* was used as a template for PCR. pSOS95-Cm can be constructed by cloning the thiolase promoter of the ATCC 824 strain into pSOS95 (Nair and Papoutsakis, J. Bacteriol., 176:5843-5846, 1994) and cloning a chloramphenicol/thiamphenicol resistance gene downstream of the promoter.

Also, after a gene was deleted by double crossover, the inserted antibiotic resistance marker should be removed for deletion of other genes. For this purpose, a mutant loxP sequence was added to primers used when amplifying $Th^r$ by PCR. Also, for ligation with a vector, the sequences GCATGC and TCTAGA of the restriction enzyme sites SphI and XbaI were added to the primers, respectively. The final primer sequences are shown by SEQ ID NOS: 8 and 9.

[SEQ ID NOS: 8]:
5'-AATTGCATGCTACCGTTCGTATAATGTATGC

TATACGAAGTTATCACACGGT TTAACGACTTAATTACG-3'

[SEQ ID NOS: 9]:
5'-ATATTCTAGAACCGTTCGTATAGCATACAT

TATACGAAGTT ATCCATGATTACGAA TTCTATGAGTCGAC-3'

PCR amplification was performed using the above template and primers, thus obtaining a PCR product comprising both the mutant loxP site and $Th^r$. The PCR product thus obtained and a pUC18 plasmid were digested with SphI/XbaI, and then ligated to each other, thus preparing the vector pMBKOT2. The pMBKOT2 vector was used in the construction of a KO cassette comprising the loxP-Thr-loxP portion and homologous arm of the pMBKOT2.

4-2: Construction of pCACKO Vector

Gene deletion by homologous recombination is generally performed using a plasmid that is not replicated in cells. However, in the case of *Clostridium acetobutylicum*, it is known that the ratio of transformation is very lower than that in *E. coli*, and homologous recombination does not easily occur. For this reason, a replicable plasmid is preferably used. Thus, a vector that can delete a specific gene was constructed using the pMBKOT2 constructed in Example 4-1 and the shuttle vector pIMP1 (Nair and Papoutsakis, J. Bacteriol., 176:5843-5846, 1994) that is replicable in *Clostridium acetobutylicum*.

The restriction enzyme sequences in pIMP1 are not suitable, except for XmaI, because they digest the inside of the loxP-$Th^r$-loxP sequence of pMBKOT2. For this reason, the restriction enzyme sequence NcoI that is not present in both pMBKOT2 and pIMP1 was added to pIMP1. PCR amplification was performed using about 300 base pairs (1155-1468 of L08752.1) located in pUC18 (GenBank ID: L08752.1), as a template, with the following primers (SEQ ID NOS: 10 and 11). The base sequence of NcoI was included in the primer of SEQ ID NO: 10.

[SEQ ID NOS: 10]:
5'-AAAACTGCAGCCATGGTCGCCAGTTAATAGTTTGCG-3'

[SEQ ID NOS: 11]:
5'-AAAACCCGGGCGCCGCATACACTATTCTCA-3'

The PCR product thus obtained and pIMP1 were digested with NcoI/XmaI, and then ligated with each other, thus constructing a pCACKO vector. Based on this vector, a gene-deleted vector was constructed.

4-3: Preparation of *Clostridium acetobutylicum* ATCC 824 ΔeutD Strain

In order to delete the eutD gene involved in the acetate-producing pathway, strands (1890304-1890770 and 1890831-1891380 of NCBI Ref Seq ID: NC_003030.1) comprising the ORF of eutD were amplified using a primer pair of SEQ ID NOS: 12 and 13 and a primer pair of SEQ ID NOS: 14 and 15, respectively. Herein, as the sequences to be amplified, templates having no NcoI and XmaI were selected. It was found that the two portions of the ORF contained in each of the amplified products did not overlap with each other and had the same orientation. Also, in order to insert a marker between the two strands, part of pMBKOT2 comprising loxP-$Th^r$-loxP was amplified using primers of SEQ ID NOS: 16 and 17.

[SEQ ID NOS: 12]:
5'-CTAGCCATGGAGCATATGGGAGTGTGCTAAG-3'

[SEQ ID NOS: 13]:
5'-CGGCCAACGCTCGCAGTCAGGTATTATCAT-3'

[SEQ ID NOS: 14]:
5'-GCGAATGGCGAGATGAACTAGCTGATATTGCTATAA-3'

-continued

[SEQ ID NOS: 15]:
5'-ACGTCCCGGGCGAGTACAGTTTCATCCTTCATATC-3'

[SEQ ID NOS: 16]:
5'-CTGACTGCGAGCGTTGGCCGATTCAT-3'

[SEQ ID NOS: 17]:
5'-TAGTTCATCTCGCCATTCGCCATTCA-3'

Overlapping PCR was performed using the three amplified strands as a template with primers of SEQ ID NOS: 12 and 15, thereby obtaining one strand. The final PCR product thus obtained and the pCACKO (KO vector) prepared in Example 4-2 were digested with NcoI/XmaI, and then ligated to each other, thereby constructing a pCACKO-eutD vector. The constructed vector was methylated, and then transformed by electroporation into the C. actobutylicum ATCC 824 strain. The transformed strain was subcultured in 2×YTGS medium while it was plated onto 2×YTG agar containing thiamphenicol. The colonies obtained from the plate were examined by colony PCR with each of a primer pair of SEQ ID NOS: 18 and 19 and a primer pair of SEQ ID NOS: 20 and 21 in order to confirm whether the Th$^r$ marker was successfully inserted in the eutD ORF.

[SEQ ID NOS: 18]:
5'-GAGGATAAAGAATATACGCAGG-3'

[SEQ ID NOS: 19]:
5'-TTGCCGTCCTAAACTCTGAA-3'

[SEQ ID NOS: 20]:
5'-CTTCCTTTGGCAATTCAAGTTC-3'

[SEQ ID NOS: 21]:
5'-GTGGATTATGAAGCGGTGCA-3'

When recombination on both sides of the gene surely occurred, the colony was cultured and plated, after which it was subjected to a degeneration test in order to verify that pSOL1 involved in solvent production was not lost. The verified strain was subcultured more than 30 times in 2×YTGS medium, after which it was plated onto 2×YTG agar containing Th and was replicated on 2×YTG agar containing erythromycin (Em), and several colonies showing no Em$^r$ were selected. The selected colonies were subjected to a degeneration test in the same manner as described above, and a colony in which pSOL1 was not lost was finally selected.

Then, pSOS95del-cre was transformed into the finally selected strain to remove the thiamphenicol resistance gene inserted in the gene. The strain was subcultured to remove pSOS95del-cre, thereby preparing a final strain (Clostridium acetobutylicum ATCC 824 ΔeutD) which is sensitive to antibiotics, such as thiamphenicol and erythromycin, like a wild-type strain, and in which the eutD gene was deleted.

4-4: Alcohol Production by Recombinant Mutant Microorganisms PTA (pTHL1-Cm-IPA1) and PTA (pTHL1-Cm-IPA2)

Each of the recombinant vectors pTHL1-Cm-IPA1 and pTHL1-Cm-IPA2 constructed in Example 2 was introduced into the Clostridium acetobutylicum pta (eutD)-deleted recombinant microorganism Clostridium acetobutylicum ATCC 824 ΔeutD by the same electroporation method as that in Example 3, thereby constructing PTA (pTHL1-Cm-IPA1) and PTA (pTHL1-Cm-IPA2) strains. The pta-deleted mutant strain was constructed using a gene deletion method by homologous recombination.

The constructed recombinant mutant microorganisms PTA (pTHL1-Cm-IPA1) and PTA (pTHL1-Cm-IPA2) were cultured and their abilities to produce mixed alcohols of butanol and isopropanol were evaluated. A 30-ml test tube containing 10 ml of CGM medium was sterilized and then taken out when it reached a temperature of 80° C. or higher. Then, the test tube was charged with nitrogen gas and cooled to room temperature in an anaerobic chamber. Then, 40 μg/ml of erythromycin was added thereto and the recombinant mutant microorganisms were inoculated into the test tubes and pre-cultured under anaerobic conditions at 37° C. until they reached an absorbance of 1.0 at 600 nm. A 500-ml flask containing 200 ml of CGM medium was sterilized and then treated in the same manner as described above, after which 10 ml of the above preculture broth was inoculated into the flask and further precultured at 37° C. under anaerobic conditions until it reached an absorbance of 1.0 at 600 nm. A 5.0-L fermenter (LiFlus GX, Biotron Inc., Kyunggi-Do, Korea) containing 1.8 L of CGM medium was sterilized, and when the temperature reached 80° C. or higher, nitrogen was supplied to the fermenter at a flow rate of 0.5 vvm for 10 hours while the temperature was lowered to room temperature. Then, 40 μg/ml of erythromycin was added to the fermenter, and 200 ml of the secondarily precultured broth was inoculated into the fermenter and cultured at 32° C. and 200 rpm for 60 hours. The adjustment of the pH was performed using ammonia water. In addition, the pH was maintained at 5.0 or higher by automatically feeding ammonia water, and nitrogen was supplied at a flow rate of 0.2 vvm (air volume/working volume/minute) during the culture.

Glucose in the culture medium was measured by a glucose analyzer (model 2700 STAT, Yellow Springs Instrument, Yellow Springs, Ohio, USA). In addition, the culture medium was collected at varying time points, and the concentration of acetone in the collected culture medium was measured by gas chromatography (Agillent 6890N GC System, Agilent Technologies Inc., CA, USA) equipped with a packed column (Supelco Carbopack™ B AW/6.6% PEG 20M, 2 m×2 mm ID, Bellefonte, Pa., USA).

As a result, the recombinant strain PTA (pTHL1-Cm-IPA1) produced 12 g/L of butanol and 4 g/L of isopropanol, and the recombinant strain PTA (pTHL1-Cm-IPA2) produced 13 g/L pf butanol and 4 g/L of isopropanol.

Example 5

Production of Alcohol Mixture of Butanol, Ethanol, and Isopropanol by Recombinant Mutant Microorganisms Each of the recombinant vectors pTHL1-Cm-IPA1 and pTHL1-Cm-IPA2 was introduced into Clostridium acetobutylicum BKM19 (KCTC 11555BP), which produces more than 10 g/l of each of ethanol and butanol by evolution, by the same electroporation method as in Example 3, thereby constructing BKM19 (pTHL1-Cm-IPA1) and BKM19 (pTHL1-Cm-IPA2) strains. The recombinant microorganisms BKM19 (pTHL1-Cm-IPA1) and BKM19 (pTHL1-Cm-IPA2) were cultured in the same manner as described in Example 4, and their abilities were evaluated. As a result, the recombinant strain BKM19 (pTHL1-Cm-IPA1) produced 14.2 g/L of butanol, 12.2 g/l of ethanol and 2.7 g/L of isopropanol. The other recombinant strain BKM19 (pTHL1-Cm-IPA2) produced 15.3 g/l of butanol, 7 g/l of ethanol, and 4.4 g/l of isopropanol.

Example 6

Removal of Acetone by Recombinant Plasmid

Clostridium acetobutylicum strains have the property of producing the byproduct acetone in addition to the alcohols butanol and ethanol. Butanol and ethanol can be used as biofuel, but acetone cannot be used as biofuel. In this case, it is required to reduce the production of acetone or remove acetone. For this purpose, the recombinant strains PTA (pTHL1-Cm-IPA1), PTA (pTHL1-Cm-IPA2), BKM19 (pTHL1-Cm-IPA1) and BKM19 (pTHL1-Cm-IPA2) constructed in Examples 4 and 5 were cultured in the same manner as described in Example 4, and their abilities to remove acetone were observed.

As a result, in the control PTA (pTHL1-Cm), the concentration of acetone started to increase gradually after the organic solvent-producing stage approached, and acetone was produced at a final concentration of about 7 g/l. On the other hand, in the recombinant strains PTA (pTHL1-Cm-IPA1) and PTA (pTHL1-Cm-IPA2), even after the organic solvent-producing stage approached, acetone was removed while it was produced, comparable with the control strain, and the two strains all had a final acetone concentration of about 3-4 g/l, which shows an acetone removal rate of about 50%.

Meanwhile, in the BKM19 (pTHL1-Cm-IPA1) and BKM19 (pTHL1-Cm-IPA2) strains, no acetone accumulation was observed throughout the culture process, and the final concentration of acetone was observed to be 0.3-0.4 g/l in the two strains. This indicates that the use of the recombinant plasmid according to the present invention shows an acetone removal rate of about 91-93%, whereas the control strain BKM19 (pTHL1-Cm) produces about 4.4 g/l of acetone.

Example 7

Induction of Mutation in Recombinant Strains

A mutation was induced in a homologous recombinant strains in which the acetic acid biosynthetic pathway of the *Clostridium acetobutylicum* ATCC 824 strain was blocked, a homologous recombinant strain in which the butyric acid biosynthetic pathway was blocked, and a homologous recombinant strain in which the lactic acid biosynthetic pathway was blocked. The above strains were constructed using a gene deletion method by homologous recombination. Three microbial cells of each of the strains were inoculated into 10 ml of 2×YTG medium (per liter, 16 g of bacto tryptone, 10 g of yeast extract, 4 g of NaCl, and 5 g of glucose) and cultured in an anaerobic chamber at 37° C. until an O.D. of 1.0 was reached. After completion of the culture, the microbial cells were collected by centrifugation and suspended in 3 ml of 2×YTG medium, and 1 ml of the suspension was dispensed into each of three 1.5-ml tubes. Then, the microorganisms were mutated with an N-methyl-N'-nitro-N-nitrosoguanidine (NTG) stock, prepared at 100 mg/ml, for 5 minutes to final concentrations of 200, 500 and 1000 ug/ml. The mutated microorganisms were collected by centrifugation and washed three times with 2×YTG medium. The washed microorganisms were suspended in 1 ml of 2×YTG medium and $10^7$-fold diluted, and the dilution was plated on 2×YTG solid medium containing 40 ug/ml of erythromycin and was cultured at 37° C. under anaerobic conditions for 5 days. After completion of the culture, the colonies were inoculated into CGM medium (Table 1) containing erythromycin and were cultured at 37° C. under anaerobic conditions for 48 hours. After completion of the culture, the supernatant was collected, and the concentration of acetic acid, butyric acid, acetone, ethanol and butanol in the collected supernatant were measured by gas chromatography (Agilent 6890N GC System, Agilent Technologies Inc., CA, USA) equipped with a packed column (Supelco Carbopack™ B AW/6.6% PEG 20M, 2 m×2 mm ID, Bellefonte, Pa., USA). The results of the measurement are shown in Table 2 below.

TABLE 2

Metabolites (g/l) of primary mutant strains

| Orders (#) | Butanol | Ethanol | Acetone | Acetic acid + Butyric acid |
|---|---|---|---|---|
| 101 | 3.5 | 1.7 | 1.5 | 7.72 |
| 102 | 5.8 | 2.2 | 2.2 | 6.14 |
| 103 | 8.2 | 3.5 | 2.2 | 3.98 |
| 104 | 9.3 | 9.2 | 0.4 | 2.06 |
| 105 | 10.8 | 6.9 | 0.5 | 1.89 |
| 106 | 6.5 | 5.1 | 1.9 | 2.23 |
| 107 | 7.0 | 3.3 | 0.7 | 5.48 |
| 108 | 6.6 | 2.9 | 2.2 | 4.46 |

The control strain produced about 3 g/l of ethanol and about 8 g/l of butanol. On the other hand, as can be seen in Table 2 above, the primary mutant strains produced various concentrations of acetic acid, butyric acid, butanol, acetone, and ethanol.

Among the primary mutant strains, the strain #104 (*Clostridium acetobutylicum* BKM19, Accession No. KCTC11555BP) having increased ethanol concentration was treated in the same manner as described above in order to induce a secondary mutation, and the metabolites thereof were analyzed. The results of the analysis are shown in Table 3 below.

TABLE 3

Metabolites (g/l) of secondary mutant strains

| Orders (#) | Butanol | Ethanol | Acetone |
|---|---|---|---|
| 201 | 8.7 | 7.0 | 1.3 |
| 202 | 8.2 | 6.7 | 1.2 |
| 203 | 10.0 | 8.4 | 1.3 |
| 204 | 9.5 | 7.8 | 1.4 |
| 205 | 8.0 | 6.5 | 1.2 |
| 206 | 9.7 | 8.6 | 1.3 |
| 207 | 10.9 | 8.3 | 1.6 |
| 208 | 7.4 | 4.9 | 1.7 |
| 209 | 6.4 | 5.0 | 0.7 |
| 210 | 5.2 | 3.4 | 0.6 |
| 211 | 3.3 | 2.5 | 0.6 |
| 212 | 5.9 | 4.3 | 0.8 |

As can be seen in Table 3 above, the secondary mutant strains also produced various concentrations of butanol, ethanol and acetone.

Example 8

Production of High Concentrations of Butanol and Ethanol by Mutant Microorganisms Among the mutant strains constructed in Example 7, the strain #104 (*Clostridium acetobutylicum* BKM19, Accession No. KCTC 11555BP) and the strain #207 (*Clostridium acetobutylicum* JA94) were examined for the ability to produce butanol and ethanol. A 30-ml test tube containing 10 ml of CGM medium was sterilized and then taken out when it reached a temperature of 80° C. or higher. Then, the test tube was charged with nitrogen gas and cooled to room temperature in an anaerobic chamber. Then, 40 μg/ml of erythromycin was added thereto and the recombinant mutant microorganisms were inoculated into the test tubes and precultured under anaerobic conditions at 37° C. until they reached an absorbance of 1.0 at 600 nm. A 500-ml flask containing 200 ml of CGM medium was sterilized and then treated in the same manner as described above, after which 10 ml of the above preculture broth was inoculated into the flask and further precultured at 37° C. under anaerobic conditions until it reached an absorbance of 1.0 at 600 nm. A 5.0-L fermenter (LiFlus GX, Biotron Inc., Kyunggi-Do, Korea) containing 1.8 L of CGM medium was sterilized, and when the temperature reached 80° C. or higher, nitrogen was supplied to the fermenter at a flow rate of 0.5 vvm for 10 hours while the temperature was lowered to room temperature. Then, 40 μg/ml of erythromycin was added to the fermenter, and 200 ml of the secondarily precultured broth was inoculated into the fermenter and cultured at 32° C. or 37° C. and 200 rpm for 60 hours. The adjustment of the pH was performed using ammonia water. In addition, the pH was maintained at 5.0 or higher by automatically feeding ammonia water, and nitrogen was supplied at a flow rate of 0.2 vvm (air volume/working volume/minute) during the culture.

Glucose in the culture medium was measured by a glucose analyzer (model 2700 STAT, Yellow Springs Instrument, Yellow Springs, Ohio, USA). In addition, the culture medium was collected at varying time points, and the concentration of acetone in the collected culture medium was measured by gas chromatography (Agillent 6890N GC System, Agilent Technologies Inc., CA, USA) equipped with a packed column (Supelco Carbopack™ B AW/6.6% PEG 20M, 2 m×2 mm ID, Bellefonte, Pa., USA).

As a result, it could be seen that, in the fermentation process at 37° C., the mutant microorganism #104 produced about 11.2-13.2 g/l of butanol, about 8.5-12.1 g/l of ethanol, and about 4.3-4.8 g/l of acetone, and in the fermentation process at 32° C., the mutant microorganism #104 produced 17.6 g/l of butanol, 10.5 g/l of ethanol, and 4.4 g/l of acetone. This indicates 28.1 g/l of an alcohol mixture of butanol and ethanol (BE) and 32.5 g/l of acetone-butanol-ethanol (ABE), which are the highest BE and ABE concentrations reported to date.

In addition, it was observed that the mutant microorganism #207 produced 19.9 g/l of butanol, 5.0 g/l of ethanol, and 5.0 g/l of acetone in the fermentation process at 32° C. This indicates a butanol concentration of about 20 g/l which is the highest butanol concentration reported to date.

Example 9

Removal of Acetone and Production of High Concentrations of Butanol, Ethanol, and Isopropanol in Recombinant Mutant Microorganisms Introduced with Gene that Encodes Enzyme Involved in Isopropanol Biosynthesis In order to reduce the production of acetone (convert acetone to isopropanol) in the mutant microbial strain #104, the plasmids pTHL1-Cm-IPA1 and pTHL1-Cm-IPA2 prepared in Example 2 were transformed in the following manner. First, each of the recombinant vectors constructed in Example 2 was introduced into E. coli TOP10 containing the Bacillus subtilis Phage Φ3T I methyltransferase expression vector pAN1 (Mermelstein et al., Appl. Environ. Microbiol., 59:1077, 1993), thereby inducing the methylation of the vectors so as to make the vectors suitable for transformation into Clostridium. Each of the methylated vectors was separated and purified from the E. coli strain and introduced into the recombinant mutant microorganism strain #104.

Competent cells for transformation were prepared in the following manner. First, the strain #104 was inoculated into 10 ml of CGM (see Table 1), and then cultured until an O.D. of 0.6 was reached. Then, the strain was inoculated into 60 ml of 2×YTG medium (per liter, 16 g of bacto tryptone, 10 g yeast extract, 4 g of NaCl, and 5 g of glucose) at a concentration of 10% and cultured for 4-5 hours. The microbial cells were washed twice with transformation buffer (EPB, 15 ml of 270 mM sucrose, 110 μl of 686 mM $NaH_2PO_4$, pH 7.4), and then suspended in 2.4 ml of the same buffer. 600 μl of the competent cells thus made were mixed with 25 μl of the recombinant plasmid DNA, and the mixture was loaded into a cuvette having a 4 mm electrode gap, and then subjected to electric shock at 2.5 kV and 25 uF. Then, the cells were immediately suspended in 1 ml of 2×YTG medium and cultured at 37° C. for 3 hours, after which the cells were plated on a 2×YTG solid medium containing 40 μg/ml of erythromycin and 5 μg/ml of chloramphenicol, and transformants were selected. The selected recombinant mutant microorganisms #104 (pTHL1-Cm-IPA1) and #104 (pTHL1-Cm-IPA2) were cultured in the same manner as described in Example 8, and their abilities to remove acetone and produce alcohols were evaluated. As a result, it could be seen that the two microorganisms all reduced the concentration of acetone to 0.3-0.4 g/l. In addition, it was seen that the strain #104 (pTHL1-Cm-IPA1) produced an alcohol mixture of butanol-ethanol-isopropanol (BEI) up to a concentration of 29.1 g/l and that the strain #104 (pTHL1-Cm-IPA2) produced an alcohol mixture of butanol-ethanol-isopropanol (BEI) up to a concentration of 26.7 g/l.

Example 10

Preparation of Recombinant Mutant Microorganism in which Gene that Encodes Enzyme Involved in Acetone Biosynthesis was Further Amplified in Strain Introduced with Gene that Encodes Enzyme Involved in Isopropanol Biosynthesis In order to increase the metabolic flux to acetone, the acetoacetate decarboxylase-encoding gene (adc) and CoA transferase-encoding gene (ctfA, ctfB) of C. acetobutylicum ATCC 824 were cloned into the shuttle vector pTHL1-Cm. Herein, the promoter used was the promoter of the acetoacetate decarboxylase-encoding gene, and each of the genes used was the RBS thereof. It is known that the adc promoter is strongly expressed in the solventogenic phase (Tummala et al., Appl. Environ. Microbiol., 65:3793~3799, 1999). First, PCR was performed using the total DNA of C. acetobutylicum ATCC 824 as a template with primers of SEQ ID NOS: 22 and 23, thereby amplifying an adc gene fragment comprising the adc promoter and RBS. In addition, a ctfAB gene fragment was amplified by PCR using the total DNA of C. acetobutylicum ATCC 824 as a template with primers of SEQ ID NOS: 24 and 25.

[SEQ ID NOS: 22]:
5'-ATATGGATCCAAGTGTACTTTTATTTTCGAAAGC-3'

[SEQ ID NOS: 23]:
5'-AATCCCTCCTTTCCATTTAAGGTAACTCTTATTTTTA-3'

[SEQ ID NOS: 24]:
5'-GTTACCTTAAATGGAAAGGAGGGATTAAAATGAACTCT-3'

[SEQ ID NOS: 25]:
5'-ATATACGCGTCTAAACAGCCATGGGTCTAA GTT-3'

Then, PCR was performed using a mixture of the PCR products of the adc gene and the ctfAB gene as a template with primers of SEQ ID NOS: 22 and 25, thereby amplifying an artificial acetone operon strand in which the adc gene and the ctfAB gene are expressed by the adc promoter. The amplified product was treated with BamHI and MluI restriction enzymes, and then ligated by T4 DNA ligase with the pTHL1-Cm vector treated with the same restriction enzymes, thereby preparing the recombinant plasmid pACT.

In addition, the primary/secondary dehydrogenase-encoding gene, the adc promoter and the adc terminator were cloned. First, in order to insert the adc terminator and the EagI restriction enzyme sequence, primers of SEQ ID NOS: 26 and 27 were complementarily bound to each other, and then ligated by T4 DNA ligase with the above product and the pUC18 vector treated with BamHI and EcoRI restriction enzymes, thereby preparing the recombinant plasmid pUCadcT.

```
[SEQ ID NOS: 26]:
5'-GATCCACTACGGCCGTAAAAATAAGAGTTACC

TTAAATG GTAACTCTTATTTTTTTAATGC-3'

[SEQ ID NOS: 27]:
5'-AATTGCATTAAAAAAATAAGAGTTACCATTT

AAGGTAACTCTTATTTTTACGGCCGTAGTG-3'
```

Furthermore, PCR was performed using the total DNA of *C. acetobutylicum* ATCC 824 as a template with primers of SEQ ID NOS: 28 and 29, thereby amplifying an adc promoter fragment which does not contain the RBS of adc. Then, the amplified product was treated with the restriction enzymes PstI and BamHI, after which it was ligated by T4 DNA ligase with the pUCadcT vector treated with the same restriction enzymes, thereby constructing the recombinant plasmid pUCadcPT.

```
[SEQ ID NOS: 28]:
5'-ATATCTGCAGAAGTGTACTTTTATTTTCGAAAGC-3'

[SEQ ID NOS: 29]:
5'-ATATGGATCCTAATAATGTTTAGCTTTTCTAACAT-3'
```

In order to insert the primary/secondary alcohol dehydrogenase- and electron transfer protein-encoding genes, each containing the inherent RBS, into the constructed pUCadcPT plasmid, PCR was performed using the total DNA of *C. beijerinckii* NRRL B-593 with a primer pair of SEQ ID NOS: 30 and 31 and a primer pair of SEQ ID NOS: 30 to 32, thereby amplifying adhI and adhI-hydg fragments, respectively.

```
[SEQ ID NOS: 30]:
5'-ATAT GGATCCTAAGGAGGAACATATTTTATGAAAG-3'

[SEQ ID NOS: 31]:
5'-ATATCGGCCGTTATAATATAACTACTGCTTTAATTA-3'

[SEQ ID NOS: 32]:
5'-ATATCGGCCGTTATTTATCACCTCTGCAACC AC-3'
```

Each of the two amplified products was treated with BamHI and EagI restriction enzymes, and then ligated by T4 DNA ligase with the pUCadcPT vector treated with the same restriction enzymes, thereby preparing the recombinant plasmids pSADH1 and pSADH2, respectively.

In order to insert the primary/secondary alcohol dehydrogenase- and electron transfer protein-encoding genes, each containing the adc promoter and terminator bound thereto, into the pACT vector, PCR was performed using each of pSADH1 and pSADH2 as a template with primers of SEQ ID NOS: 33 and 34. Then, each of the two amplified products was treated with SphI and XmaI restriction enzymes and ligated by T4 DNA ligase with the pACT vector treated with the same restriction enzymes, thereby constructing the recombinant plasmids pIPA3 and pIPA4, respectively.

```
[SEQ ID NOS: 33]:
5'-CGGGCCTCTTCGCTATTACG-3'

[SEQ ID NOS: 34]:
5'-ATATCCCGGGGAATTGTGAGCGGATAACA-3'
```

Each of the constructed pIPA3 and pIPA4 were methylated in the same manner as described in Example 3, and was then introduced into *Clostridium acetobutylicum* BKM19 (KCTC 11555BP) which produces 10 g/l or more of each of ethanol and butanol by evolution, thereby constructing the recombinant mutant microorganisms BKM19 (pIPA3) and BKM19 (pIPA4).

Example 11

Production of High Concentrations of Mixed Alcohols in Recombinant Mutant Microorganism in which Gene that Encodes Enzyme Involved in Acetone Biosynthesis was Further Amplified in Strain Introduced with Gene that Encodes Enzyme Involved in Isopropanol Biosynthesis The recombinant mutant microorganisms BKM19 (pIPA3) and BKM19 (pIPA4) constructed in Example 10 were cultured in the same manner as described in Example 4, and their abilities to remove acetone and produce alcohols were evaluated. As a result, it was seen that, in the strain BKM19 (pIPA3), the acetone concentration was maintained at about 0.5 g/l, even though the acetone biosynthetic pathway was amplified. In addition, the strain BKM19 (pIPA3) produced 5.6 g/l of ethanol, 5.2 g/l of isopropanol, and 18.5 g/l of butanol, indicating that the total production of mixed alcohols reached 29.3 g/l. Moreover, the ability of the strain BKM19 (pIPA4) to produce acetone, ethanol, isopropanol and butanol was very similar to that of the strain BKM19 (pIPA3). These strains show the highest BEI concentration reported to date and have a characteristic in that the ratio of butanol in mixed alcohols is high.

INDUSTRIAL APPLICABILITY

As described above, the present invention provides a recombinant mutant microorganism which has an increased ability to produce butanol, ethanol, isopropanol or mixed alcohols through the amplification or introduction of specific genes in host microorganisms, and a recombinant mutant microorganisms which has an increased ability to produce butanol, ethanol, and isopropanol through evolution using manipulation of metabolic pathways and mutation. The recombinant mutant microorganisms according to the present invention produce little or no byproducts such as acetone and can have an increased ability to produce alcohols, as a result of manipulating metabolic pathways. Thus, the recombinant mutant microorganisms are useful for industrial production of butanol, ethanol, isopropanol, or mixed alcohols Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A recombinant mutant microorganism having (A) an increased ability to produce butanol or mixed alcohols and (B) an increased ability to remove acetone, wherein the genes that encode enzymes involved in producing butanol from butyryl-CoA or butyraldehyde and involved in producing isopropanol from acetone are introduced in a host microorganism of the genus *Clostridium*, wherein the genes that encode enzymes involved in producing butanol from butyryl-CoA or butyraldehyde and involved in producing isopropanol from acetone are a primary/secondary alcohol dehydrogenase-encoding gene (adhI) and an electron-transfer protein-encoding gene (hydG).

2. The recombinant mutant microorganism of claim 1, wherein the adhI and the hydG are derived from *Clostridium beijerinckii* NRRL B593.

3. The recombinant mutant microorganism of claim 1, wherein the mixed alcohols comprise butanol and isopropanol.

4. The recombinant mutant microorganism of claim 1, wherein the host microorganism comprises one or more metabolic pathways selected from the group consisting of: (A) an acetyl-CoA biosynthetic pathway; (B) a butyryl-CoA biosynthetic pathway; (C) an acetone biosynthetic pathway; (D) an ethanol biosynthetic pathway; (E) a butanol biosynthetic pathway; (F) an isobutanol biosynthetic pathway; (G) a propanol biosynthetic pathway; and (H) an isopropanol biosynthetic pathway.

5. The recombinant mutant microorganism of claim 1, wherein the host microorganism is one in which one or more biosynthetic pathways selected from the group consisting of: (A) an acetic acid biosynthetic pathway; (B) a butyric acid biosynthetic pathway; (C) a lactic acid biosynthetic pathway; (D) an acetoin biosynthetic pathway; and (E) a hydrogen biosynthetic pathway were completely blocked or regulated.

6. The recombinant mutant microorganism of claim 1, further comprising amplifying or introducing genes that encode enzymes involved in acetone biosynthesis, wherein the genes that encode enzymes involved in acetone biosynthesis are selected from the group consisting of an acetoacetate decarboxylase-encoding gene (adc) and a CoA transferase-encoding gene (ctfA, ctfB).

7. The recombinant mutant microorganism of claim 1, wherein the host microorganism is *Clostridium acetobutylicum* BKM 19.

8. A method of preparing a recombinant mutant microorganism having (A) an increased ability to produce butanol or mixed alcohols and (B) an increased ability to remove acetone, the method comprising introducing genes, which encode enzymes involved in producing butanol from butyryl-CoA or butyraldehyde and involved in producing isopropanol from acetone, in a host microorganism of the genus *Clostridium*, wherein the genes that encode enzymes involved in producing butanol from butyryl-CoA or butyraldehyde and involved in producing isopropanol from acetone are a primary/secondary alcohol dehydrogenase-encoding gene (adhI) and an electron-transfer protein-encoding gene (hydG).

9. The method of claim 8, wherein the adhI and the hydG are derived from *Clostridium beijerinckii* NRRL B593.

10. The method of claim 8, wherein the mixed alcohols comprise butanol and isopropanol.

11. The method of claim 8, wherein the host microorganism comprises one or more metabolic pathways selected from the group consisting of: (A) an acetyl-CoA biosynthetic pathway; (B) a butyryl-CoA biosynthetic pathway; (C) an acetone biosynthetic pathway; (D) an ethanol biosynthetic pathway; (E) a butanol biosynthetic pathway; (F) an isobutanol biosynthetic pathway;
(G) a propanol biosynthetic pathway; and (H) an isopropanol biosynthetic pathway.

12. The method of claim 8, wherein the host microorganism is one in which one or more biosynthetic pathways selected from the group consisting of: (A) an acetic acid biosynthetic pathway; (B) a butyric acid biosynthetic pathway; (C) a lactic acid biosynthetic pathway; (D) an acetoin biosynthetic pathway; and (E) a hydrogen biosynthetic pathway were completely blocked or regulated.

13. The method of claim 8, further comprising amplifying or introducing genes that encode enzymes involved in acetone biosynthesis, wherein the genes that encode enzymes involved in acetone biosynthesis are selected from the group consisting of an acetoacetate decarboxylase-encoding gene (adc) and a CoA transferase-encoding gene (ctfA, ctfB).

14. A method for producing butanol or mixed alcohols, the method comprising: culturing the recombinant mutant microorganism of claim 1 to produce butanol or mixed alcohols; and then recovering butanol or mixed alcohols from a culture medium used in the culture of the microorganism.

15. The method of claim 8, wherein the host microorganism is *Clostridium acetobutylicum* BKM19.

16. A method for producing butanol or mixed alcohols, the method comprising: culturing the recombinant mutant microorganism of claim 6 to produce butanol or mixed alcohols; and then recovering butanol or mixed alcohols from a culture medium used in the culture of the microorganism.

* * * * *